United States Patent [19]

Chodnekar et al.

[11] 3,966,780

[45] June 29, 1976

[54] PROPARGYL ESTERS OF 7,11-SUBSTITUTED DODECADIENOIC ACIDS

[75] Inventors: Madhukar Subraya Chodnekar, Basel; Peter Loeliger; Albert Pfiffner, both of Pfaffhausen; Ulrich Schwieter, Reinach; Milos Suchy; René Zurflüh, both of Pfaffhausen, all of Switzerland

[73] Assignee: Hoffmann-La Roche Inc., Nutley, N.J.

[22] Filed: June 8, 1973

[21] Appl. No.: 368,135

[30] Foreign Application Priority Data
June 16, 1972 Switzerland.......................... 9109/72
June 29, 1972 Switzerland.......................... 9744/72

[52] U.S. Cl...................... 260/410.9 N; 260/404; 260/410.9 R; 260/348 R; 260/348 A; 260/455 R; 260/465.1; 260/465.6; 260/479 C; 260/593 R; 260/594; 260/601 R; 260/602; 260/614 R; 260/615 R; 424/278; 424/300; 424/301; 424/304; 424/312; 424/320; 424/332; 424/333; 424/339

[51] Int. Cl.²..................... C07C 69/61; A01N 9/24

[58] Field of Search.............. 260/410.9 R, 410.9 N, 260/348 A

[56] References Cited
UNITED STATES PATENTS

| | | |
|---|---|---|
| 3,706,733 | 12/1972 | Henrick.......................... 260/327 E |
| 3,716,565 | 2/1973 | Henrick et al............... 260/410.9 R |
| 3,752,843 | 8/1973 | Henrick........................... 260/465.9 |
| 3,755,411 | 8/1973 | Henrick et al.................. 260/465.6 |
| 3,773,793 | 11/1973 | Henrick........................... 260/343.5 |
| 3,773,797 | 11/1973 | Chodnekar et al............ 260/348 R |
| 3,839,562 | 10/1974 | Chodnekar et al................. 424/187 |

FOREIGN PATENTS OR APPLICATIONS 2,115,673  10/1971  Germany

OTHER PUBLICATIONS

Heinz et al., J. Food Sci., 31, pp. 69–80, (1966).

Kamal et al. (I), Chemical Abstracts, vol. 75, 126859d (1971).

Kamal et al. (II), Chemical Abstracts, vol. 75, 126877h (1971).

Burden et al., J. Chem. Soc. (C), pp. 2477–2481 (1969).

*Primary Examiner*—Nicholas S. Rizzo
*Assistant Examiner*—Diana G. Rivers
*Attorney, Agent, or Firm*—Samuel L. Welt; Bernard S. Leon; Richard A. Gaither

[57] ABSTRACT

Polyene esters, ethers, carbamates, thioesters, amides, carbonyls and nitriles, containing at least one pair of conjugated double bonds, which are useful in killing pests, such as insects, and preventing the proliferation of such pests by upsetting their hormonal balance.

9 Claims, No Drawings

PROPARGYL ESTERS OF 7,11-SUBSTITUTED DODECADIENOIC ACIDS

SUMMARY OF THE INVENTION

In accordance with this invention, it has been discovered that polyene compounds of the formula:

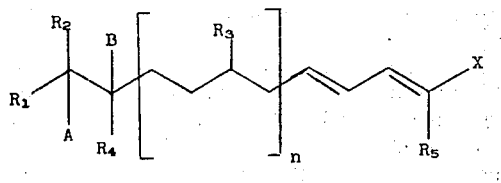

wherein $R_1$ is lower alkyl; $R_2$, $R_3$, $R_4$ and $R_5$ are hydrogen or lower alkyl; A is individually hydrogen, hydroxy, lower alkoxy or lower alkyl; B is individually hydrogen; or A and B taken together form a carbon to carbon double bond or an oxygen bridge; X is $-COOR_6$, $-CH_2OR_6$, $-CH_2O-CONH-R_7$, $-COSR_6$,

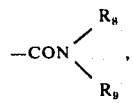

$-COR_{10}$ or $-CN$; $R_6$ is lower alkyl, lower alkenyl or lower alkynyl; $R_7$ is hydrogen or lower alkyl; $R_8$ and $R_9$ are hydrogen or lower alkyl; $R_{10}$ is hydrogen, lower alkyl, lower alkenyl or lower alkynyl; and $n$ is an integer from 0 to 1; with the proviso that when $n$ is 1, $R_3$ is lower alkyl and $R_5$ is hydrogen, then X is $-COOR_6$, $-CH_2OR_6$, $-CH_2O-CONH-R_7$, $-COSR_6$ or $-COR_{10}$ and $R_6$ and $R_{10}$ are lower alkenyl or lower alkinyl, upset the hormone balance of pests such as insects to prevent them from growing and reproducing. The compounds of formula I can be utilized in pesticide compositions which can be applied to various substrates to keep them free from pests.

DETAILED DESCRIPTION OF THE INVENTION

As used throughout this application, the term lower alkyl comprehends straight chain and branched chain, saturated aliphatic hydrocarbon groups containing 1–6 carbon atoms, such as methyl, ethyl, propyl, isopropyl, pentyl, and 3-pentyl. The preferred lower alkyl group is methyl. Also, in this application, the term lower alkenyl comprehends straight chain and branched chain, aliphatic hydrocarbon groups, containing 2–6 carbon atoms and one or more carbon to carbon double bonds, such as vinyl, allyl, butenyl and pentenyl. Further in this application, the term lower alkynyl comprehends straight chain and branched chain, aliphatic hydrocarbon groups, containing 2–6 carbon atoms and one or more carbon to carbon triple bonds, such as ethynyl, propargyl and butynyl.

As also used throughout this application, the term halogen includes fluorine, chlorine, bromine and iodine, unless expressly stated otherwise. Also herein, the term alkali metal includes lithium, sodium, potassium, rubidium and caesium, unless expressly stated otherwise. Further herein, the term alkaline earth metal includes beryllium, magnesium, calcium, strontium and barium, unless expressly stated otherwise. Still further herein, the term lower alkoxy comprehends lower alkoxy groups wherein the lower alkyl moiety is as defined above, such as methoxy, propoxy and pentyloxy.

As further used throughout this application, the term aryl includes mono-nuclear aryl groups, such as phenyl, which can be unsubstituted or substituted in one or more positions with a lower alkyl, halogen, lower alkoxy, amino, nitro, mono- or di-lower alkylamino moiety, as well as polynuclear aryl groups, such as naphthyl, anthryl, phenanthryl, and azulyl, which may be unsubstituted or substituted with one or more of the aforementioned moieties. The preferred aryl groups are the phenyl, halophenyl and lower alkoxy phenyl groups. Also herein, the term dilower alkylamino includes dilower alkylamino groups wherein the lower alkyl moieties contain from 1 to 6 carbon atoms such as methyl, ethyl, isopropyl, etc.

The polyene compounds of formula I are useful for the control of pests, especially invertebrate animals, particularly Arthropoda and Nematoda. In contrast to most of the known pesticides, which kill, disable or repel as contact or feed poisons, the polyene compounds of formula I act on the hormonal system of the animal organism. In insects, for example, the metamorphosis to the imago, the laying of viable eggs and the development of laid, normal eggs are disrupted. The sequence of insect generation is interrupted, and thereby, the insects are indirectly killed.

The polyene compounds of formula I are practically non-toxic to vertebrate animals. The toxicity of the polyene compounds of formula I lies at over 1000 mg/kg body weight. Moreover, these compounds are easily degraded, and the risk of accumulation is thereby eliminated. Therefore, the polyene compounds of the formula I can be used unhesitatingly for the control of pests in animals, plants, foods and textiles.

Among the Arthropoda and Nematoda against which the polyene compounds of this application are especially useful are included: Blattidae, Psocoids, Thysanopteroids, Hemiptera, Hymenoptera, Choleoptera, Diptera, Lepidoptera and Neuroptera, particularly

| | |
|---|---|
| Metatetranychus | (red citrus spider mite), |
| Tetranychus spp. | (common spider mite), |
| Anthonomus grandis | (boll weevil), |
| Chilo suppressalis | (asiatic rice borer), |
| Diatraea saccharalis, | |
| Heliothis spp. | (bollworm), |
| Pyrausta nubilalis | (corn borer), |
| Carpocapsa pomonella | (codlin moth), |
| Ceratitis capitata | (mediterranean fruit fly), |
| Aonidiella aurantii | (red californian scale louse), |
| Aphis gossypii | (cotton aphid), |
| Myzus persicae | (peach aphid), |
| Locusta migratoria | (migratory locust), |
| Tribolium spp. | (rice flour beetle), |
| Sitophilus spp. | (grain weevil) |
| Ephestia kuhniella | (flour moth), |
| Plodia interpunctella | (dried-fruit moth), |
| Aedes spp. | (mosquitoes) |
| Anopheles spp. | (malarial mosquito), |
| Musca domestica | (house fly), |
| Stomoxys calcitrans | (stable fly calf biter), |
| Blattella germanica | (cockroach), and |
| Cochliomyia hominivorax | (screw worm). |

Generally, in controlling invertebrate animals, the compounds of formula I above thereof are applied to the material to be protected, e.g., foodstuffs, feeds, textiles, plants, in concentrations of from about $10^{-3}$ to $10^{-6}$ gm/cm$^2$ of the material to be protected. Generally, it is preferred to utilize the compounds of formula I above in a composition with a suitable inert carrier. In such compositions, any conventional inert carrier can be utilized.

The polyene compounds of formula I can, for example, be used as pesticides in the form of concentrates or as ready-to-use agents. The pesticides containing the polyene compounds of formula I can take the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them by the action of external influences (e.g., contact with moisture) or in the animal body itself.

The compounds of formula I can be used as solution suitable for spraying on the material to be protected which can be prepared by dissolving or dispersing these compounds in a solvent such as mineral oil fractions; cold tar oils; oils of vegetable or animal origins; hydrocarbons such as napthalenes; ketones such as methyl ethyl ketone; or chlorinated hydrocarbons such as tetrachloroethylene, tetrachlorobenzene, and the like. The compounds of formula I above can also be prepared in forms suitable for dilution with water to form aqueous liquids such as, for example, emulsions concentrates, pastes or powders. The compounds of formula I above can be combined with solid carriers for making dusting or strewing powders as, for example, talc, kaolin, bentonite, calcium carbonate, calcium phosphate, etc. The compositions containing the compounds of formula I above can contain, if desired, emulsifiers, dispersing agents, wetting agents, masking agents or other active substances such as fungicides, bacteriocides, nematocides, fertilizers and the like. The materials which are to be protected act as bait for the insect. In this manner, the insect, by contacting the material impregnated with a compound of formula I above, also contacts the compound itself.

In general, the polyene compounds of formula I can be formulated into pesticide compositions according to the processes described, for example, in *Farm Chemicals*, Volume 128, page 52. These pesticide compositions can be made up in the form of concentrates which are suitable for storage and transport. Such concentrates can for example contain 40–80% by weight of a polyene compound of formula I. These concentrates can also be diluted with the same or a different carrier material to provide concentrations which are suitable for practical use. In a ready-to-use pesticide (e.g. a spray), the polyene compound can, for example, be present in a concentration of 0.01–0.5% by weight, preferably 0.1% by weight. The foregoing concentrations can, however, also be smaller or larger if desired.

It will be appreciated from the foregoing that the invention herein includes within its scope pesticide compositions, which are useful for the control of pests and which contain as an essential active ingredient one or more of the polyene compounds of formula I in association with a compatible carrier material. In addition, the invention herein includes within its scope a method of rendering a locus, subject to or subjected to attack by pests, immune to or free from such attack, said method comprising applying to said locus a pesticide composition containing one or more of the polyene compounds of formula I.

In accordance with this invention, included among the preferred polyene compounds of formula I are:
7,11-dimethyl-2,4-dodecadienoic acid allyl ester,
7,11-dimethyl-2,4-dodecadienyl allyl ether,
7,11-dimethyl-2,4-dodecadienyl propargyl ether,
7,11,11-trimethyl-2,4-dodecadienoic acid propargyl ester,
7,10,11-trimethyl-2,4-dodecadienoic acid propargyl ester
7,11-dimethyl-2,4,10-dodecatrienoic acid propargyl ester,
11-methoxy-7,11-dimethyl-2,4-dodecadienoic acid propargyl ester,
11-methoxy-7,11-dimethyl-2,4-dodecadienoic acid allyl ester,
7-methyl-2,4-octadienoic acid methyl ester,
7-methyl-2,4-octadienoic acid propargyl ester,
7-methyl-2,4-octadienoic acid isopropyl ester,
2,7-dimethyl-2,4-octadienoic acid ethyl ester,
2,7-dimethyl-2,4-octadienoic acid propargyl ester,
2,7-dimethyl-2,4-octadienoic acid isopropyl ester,
2,7,11-trimethyl-2,4-dodecadienoic acid ethyl ester,
2,7,11-trimethyl-2,4-dodecadienoic acid propargyl ester,
7,11-dimethyl-2,4-dodecadienyl-methylcarbamate,
7-methyl-2,4-octadienyl-methylcarbamate,
2,7,10,11-tetramethyl-2,4,10-dodecatrienoic acid propargyl ester,
2,7,10,11-tetramethyl-2,4-dodecadienoic acid ethyl ester,
2,7,10,11-tetramethyl-2,4-dodecadienoic acid isopropyl ester,
2,7,10,11-tetramethyl-2,4-dodecadienoic acid propargyl ester,
11-methoxy-2,7,11-trimethyl-2,4-dodecadienoic acid ethyl ester,
11-methoxy-2,7,11-trimethyl-2,4-dodecadienoic acid isopropyl ester, and
11-methoxy-2,7,11-trimethyl-2,4-dodecadienoic acid propargyl ester.

In accordance with this invention, among the most preferred polyene compounds of formula I are the polyene compounds wherein X is —COOR$_6$ or —CH$_2$OR$_6$, especially the polyene compounds wherein R$_6$ is allyl or propargyl, particularly propargyl.

In accordance with this invention, also among the most preferred polyene compounds of formula I are the polyene compounds of the formula:

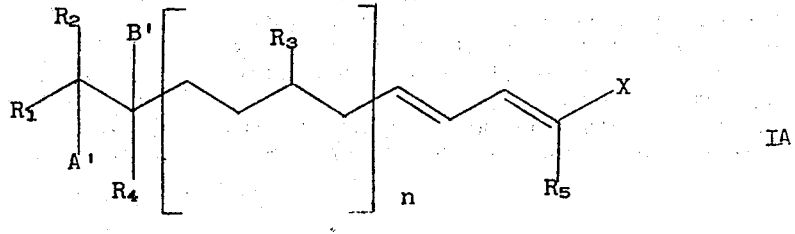

IA wherein
X, $n$, $R_1$, $R_2$, $R_3$, $R_4$ and $R_5$ are as above;
A' is hydrogen, lower alkoxy or lower alkyl; and
B' is hydrogen.

Among the polyene compounds of formula IA, especially preferred are the compounds wherein X is —COOR$_6$ or —CH$_2$OR$_6$ and R$_6$ is allyl or propargyl, quite especially propargyl. Among the especially preferred compounds of formula IA, particularly preferred are the compounds wherein R$_4$ and R$_5$ are hydrogen and the compounds wherein R$_4$ is methyl and R$_5$ is hydrogen or methyl.

In accordance with this application, further among the most preferred polyene compounds of formula I are the polyene compounds of the formula:

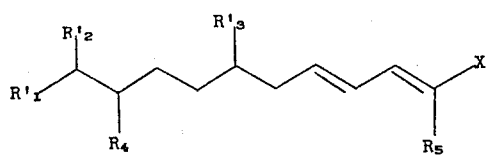

wherein
X, R$_4$ and R$_5$ are as above; and
R$_1'$, R$_2'$ and R$_3'$ are hydrogen or methyl.

Among the compounds of formula IB, especially preferred are the compounds wherein R$_4$ and R$_5$ are hydrogen or methyl. Among the especially preferred compounds of formula IB, particularly preferred are the compounds wherein X is —COOR$_6$ or —CH$_2$OR$_6$, quite particularly where R$_6$ is allyl or propargyl, quite especially propargyl.

In accordance with this application, among the most preferred polyene carbonyl compounds of formula I are the compounds wherein n is 0, especially the compounds wherein R$_{10}$ is lower alkenyl or lower alkynyl.

The polyene esters, nitriles and amides of formula I can be obtained by reacting a carbonyl compound of the formula:

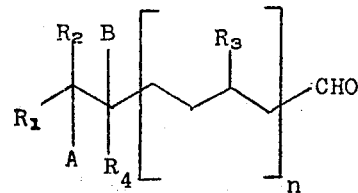

wherein R$_1$, R$_2$, R$_3$, R$_4$, $n$, A and B are as above; with a phosphine oxide of the formula:

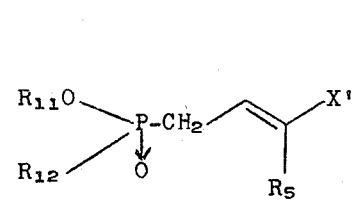

wherein
X' is —COOR$_6$, —CN or

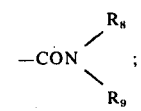

R$_5$, R$_6$, R$_8$ and R$_9$ are as above; and R$_{11}$ and R$_{12}$ are lower alkyl or aryl.

The polyene esters, nitriles and amides of formula I can also be obtained by reacting a carbonyl compound of the formula:

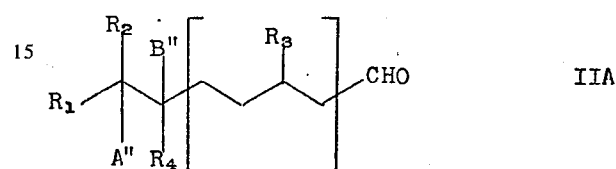

wherein
R$_1$, R$_2$, R$_3$, R$_4$ and $n$ are as above; and
A'' and B'' are individually hydrogen or taken together form a carbon to carbon double bond;
with a phosphorane of the formula:

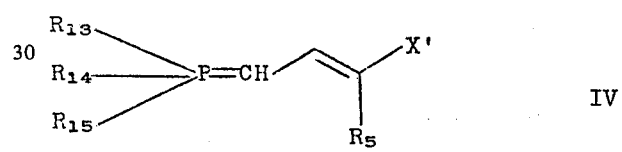

wherein
X' and R$_5$ are as above; and
R$_{13}$, R$_{14}$ and R$_{15}$ are aryl or diloweralkylamino.

The polyene esters, nitriles and amides of formula I can further be obtained by reacting a carbonyl compound of the formula:

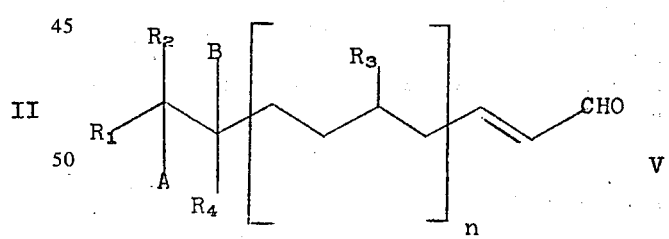

wherein R$_1$, R$_2$, R$_3$, R$_4$, $n$ A and B are as above; with a phosphine oxide of the formula:

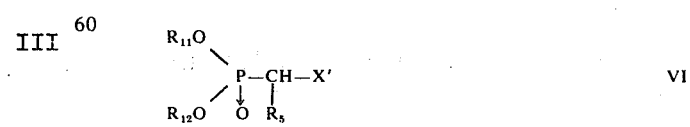

wherein R$_5$, R$_{11}$, R$_{12}$ and X' are as above.

The polyene esters, nitriles and amides of formula I can still further be obtained by reacting a carbonyl compound of the formula:

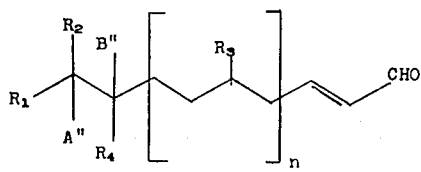   VII wherein $R_1$, $R_2$, $R_3$, $R_4$, $n$, A'' and B'' are as above; with a phosphorane of the formula:

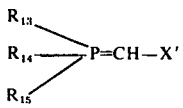   VIII wherein $R_{13}$, $R_{14}$, $R_{15}$ and X' are as above.

The polyene ethers of formula I can be obtained by reacting a compound of the formula:

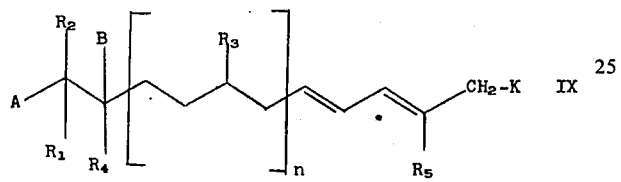   IX with a compound of the formula:

   X wherein
$R_1$, $R_2$, $R_3$, $R_4$, $R_5$, $R_6$, $n$, A and B are as above;
one of J and K is chlorine, bromine, iodine, or tosyloxy and the other is —OM; and M is an alkali metal or alkaline earth metal.

The epoxy-polyene compounds of formula I can be obtained by epoxidizing a polyene compound of formula I wherein A and B taken together form a carbon to carbon double bond.

The polyene esters, nitriles and amides of formula I can additionally be formed by: reacting a carbonyl compound of formula IIA with a compound of the formula:

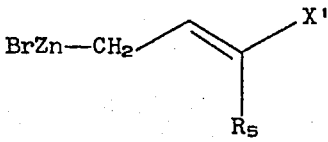   XI wherein
$R_5$ and X' are as above;
Zn is zinc; and
Br is bromine;
and dehydrating the resulting compound of the formula:

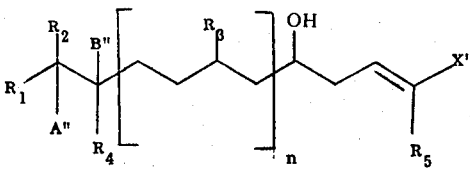   XII wherein $R_1$, $R_2$, $R_3$, $R_4$, $R_5$, A'', B'', X' and $n$ are as above.

The polyene esters, nitriles and amides of formula I can also be obtained by: reacting a carbonyl compound of formula VII with a compound of the formula:

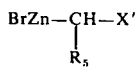   XIII wherein
$R_5$, X', Zn and Br are as above; and
dehydrating the resulting compound of the formula:

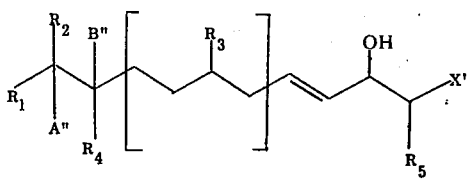   XIV wherein $R_1$, $R_2$, $R_3$, $R_4$, $R_5$, A'', B'', X', and $n$ are as above.

The polyene carbamates of formula I can be obtained by reacting a polyene alcohol of the formula:

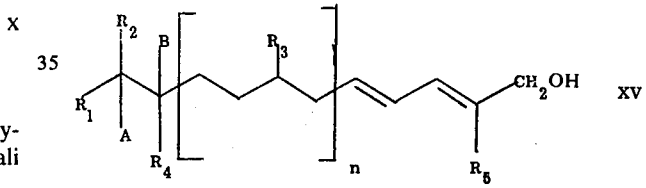   XV wherein $R_1$, $R_2$, $R_3$, $R_4$, $R_5$, A, B and $n$ are as above; with a compound of the formula:

$R_7$—N=C=O   XVI wherein $R_7$ is as above.

The polyene aldehydes of formula I, wherein $R_{10}$ is hydrogen, can be obtained by oxidizing a polyene alcohol of formula XV.

The polyene esters of formula I can further be obtained by reacting an acid of the formula:

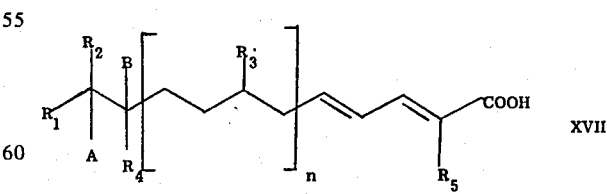   XVII wherein
$R_1$, $R_2$, $R_3$, $R_4$, $R_5$, $n$, A and B are as above;
with a halide of the formula:

$R_6$-Y   XVIII wherein $R_6$ is as above; and Y is halogen.

The polyene esters and amides of formula I can be still further obtained by converting an acid of formula XVII into the corresponding acid chloride or acid bromide and then treating the resulting acid chloride or acid bromide with an alcohol of the formula:

$R_6$-OH            XVIIIA wherein $R_6$ is as above; or with an amine of the formula:

           XIX wherein $R_8$ and $R_9$ are as above.

The polyene ketones of formula I, wherein $R_{10}$ is lower alkyl, lower alkenyl or lower alkynyl, can be obtained by reacting an acid of formula XVII with an organo-lithium compound of the formula:

$R_6$-Li            XX wherein $R_6$ is as above; and Li is lithium.

The polyene compounds of formula I wherein A is hydroxy or lower alkoxy and B is hydrogen can be obtained by reacting a polyene compound of formula I wherein A and B taken together form a carbon to carbon double bond with water or a lower alkanol in the presence of acid or a mercury salt, with the resulting organo-mercury compound being subsequently reduced.

The polyene compounds of formula I wherein A is lower alkoxy and B is hydrogen can also be obtained by reacting a polyene compound of formula I wherein A is hydroxy and B is hydrogen with a compound of the formulae:

$R_{16}$-Z            XXI wherein $R_{16}$ is lower alkyl; and X is chlorine, bromine, iodine, or tosyloxy.

The polyene esters of formula I can further be obtained in a conventional manner by re-esterification of polyene polyene ester of formula I.

The polyene amides of formula I can also be obtained in a conventional manner from a poylene ester of formula I.

The polyene thioesters of formula I can be obtained by reacting an acid chloride or acid bromide corresponding to the acid of formula XVII with a compound of the formula:

$M_1SR_6$            XXII wherein $R_6$ is as above; and $M_1$ is hydrogen, an alkali metal or an alkaline earth metal.

The polyene nitriles of formula I can be obtained by reacting a carbonyl compound of formula V with a phosphonacetonitrile of the formula:

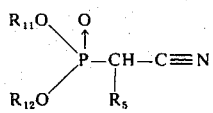
           XXIII wherein $R_5$, $R_{11}$ and $R_{12}$ are as above; in the presence of a base.

In forming the polyene compounds of formula I of this application, the preferred starting materials include:

Citronellal,
7,11-dimethyl-2,4,10-dodecatrienoic acid,
2,7,11-trimethyl-2,4,10-dodecatrienoic acid,
7,11-dimethyl-2,4,10-dodecatrien-1-ol,
2,7,11-trimethyl-2,4,10-dodecatrien-1-ol,
3,6,7-trimethyl-6-octenal,
7,10,11-trimethyl-2,4,10-dodecatrienoic acid,
2,7,10,11-tetramethyl-2,4,10-dodecatrienoic acid,
7,10,11-trimethyl-2,4,10-dodecatrien-1-ol,
2,7,10,11-tetramethyl-2,4,10-dodecatrien-1-ol,
3,7-dimethyl-7-methoxy-octan-1-ol,
7,11-dimethyl-11-methoxy-2,4-dodecadienoic acid,
2,7,11-trimethyl-11-methoxy-2,4-dodecadienoic acid,
7,11-dimethyl-11-methoxy-2,4-dodecadien-1-ol,
2,7,11-trimethyl-11-methoxy-2,4-dodecadien-1-ol,
tetrahydrocitral,
7,11-dimethyl-2,4-dodecadienoic acid,
2,7,11-trimethyl-2,4-dodecadienoic acid,
7,11-dimethyl-2,4-dodecadien-1-ol,
2,7,11-trimethyl-2,4-dodecadien-1-ol,
3,6,7-trimethyl-octan-1-ol,
7,10,11-trimethyl-2,4-dodecadienoic acid,
2,7,10,11-tetramethyl-2,4-dodecadienoic acid,
7,10,11-trimethyl-2,4-dodecadien-1-ol,
2,7,10,11-tetramethyl-2,4-dodecadien-1-ol,
3,7,7'-trimethyl-octan-1-ol,
7,11,11'-trimethyl-2,4-dodecadienoic acid,
2,7,11,11'-tetramethyl-2,4-dodecadienoic acid,
7,11,11'-trimethyl-2,4-dodecadien-1-ol,
2,7,11,11'-tetramethyl-2,4-dodecadien-1-ol,
7,11-dimethyl-11-methoxy-2,4-dodecadienoic acid thioethyl ester,
7,11-dimethyl-2,4-dodecadienoic acid thioethyl ester,
7,11-dimethyl-2,4-dodecadienoic acid thioisopropyl ester, and
2,7,11-trimethyl-2,4-dodecadienoic acid thiobutyl ester.

One method for preparing a polyene ester, nitrile or amide of this application involves reacting the carbonyl compound of formula II or V with the phosphine oxide of formula III or VI to give a corresponding polyene ester, nitrile or amide of formula I. This reaction can be carried out in a conventional manner in the presence of a base, preferably in the presence of an inert organic solvent. In this reaction, any conventional base and inert organic solvent can be utilized. The preferred bases are, however, the alkali metal hydrides, such as sodium hydride, preferably dissolved in a solvent such as benzene, toluene, dimethylformamide, tetrahydrofuran, dioxane or 1,2-dimethoxyethane, and the alkali metal alcoholates, such as sodium methylate, dissolved in an alcohol, such as methanol. Although temperature and pressure are not critical, this reaction is preferably effected between about −20°C. and the boiling temperature of the solvent, especially between about 0°C. and room temperature (22°C.), and at atmospheric pressure. In carrying out this reaction, it is especially preferred that the carbonyl compound be reacted with the phosphine oxide in the presence of 2 mol of sodium hydride in absolute tetrahydrofuran, with excess sodium hydride being decomposed by the addition of an absolute alkanol, prior to the work-up.

A second method for preparing a polyene ester, nitrile or amide of this application involves reacting the carbonyl compound of formula IIA or VII with the phosphorane of formula IV or VIII. This reaction can be carried out in a conventional manner in the presence of catalytic amounts of an organic acid. In this reaction, any conventional organic acid such as the lower alkanoic acids and benzoic acid can be utilized. Generally, this reaction is carried out in an inert organic solvent such as benzene, toluene, dimethylformamide, 1,2-dimethoxyethane or dioxane. Although temperature and pressure are not critical in this reaction, temperatures between about room temperature (22°C.) and the boiling point of the solvent and atmospheric pressure are preferred.

A method for preparing a polyene ether of this application involves reacting the alcoholate of formula IX with the halide or a tosylate of formula X or reacting the alcoholate of formula X with the halide or tosylate of formula IX.

This reaction can be carried out in a conventional manner in an inert organic solvent, such as dimethylformamide, dioxane or hexamethylphosphoric acid triamide. If desired, the alcoholate can be expediently formed in situ by carrying out the reaction in the presence of an alkali metal or alkaline earth metal, preferably sodium, or a corresponding hydride or amide, especially sodium hydride or sodium amide. Although temperature and pressure are not critical in this reaction, temperatures of between about −20°C. and the boiling temperature of the reaction mixture and atmospheric pressure are preferred. The especially preferred reaction temperature is about room temperature (22°C.), particularly when the compound of formula X is a bromide.

A method for preparing an epoxy-polyene compound of formula I, wherein A and B taken together form an oxygen bridge, involves treating the polyene compound of formula I in which A and B taken together form a carbon to carbon double bond with an epoxidizing agent. This reaction can be carried out in a conventional manner by treating the polyene compound of formula I, in inert organic solvent, with a peracid. In this reaction, any conventional inert organic solvent can be utilized, with the halogenated hydrocarbon solvents, such as chloroform or carbon tetrachloride, being preferred, particularly methylene chloride. Any conventional peracid can be utilized in this reaction, such as performic acid, peracetic acid, perbenzoic acid, perphthalic acid or pertungstic acid, with m-chloroperbenzoic acid being preferred. Although temperature and pressure are not critical in this reaction, temperatures lying between about 0°C. and room temperature (22°C.) and atmospheric pressure are preferred.

A second method for preparing an epoxy-polyene compound of formula I, wherein A and B taken together form an oxygen bridge, involves treating the polyene compound of formula I, wherein A and B taken together form a carbon to carbon double bond, with a hydroxy halogenating agent and then dehydrogenating the resulting halohydrin with a base. The hydroxyhalogenation reaction can be carried out in a conventional manner by suspending the polyene compound of formula I, in which A and B taken together form a carbon to carbon double bond, in water and mixing the suspension with an amount of an inert organic solvent. Any conventional inert organic solvent which will provide a homogeneous, concentrated solution can be utilized, such as dioxane or 1,2-dimethoxyethane, preferably, tetrahydrofuran. The resulting solution can then be treated in a conventional manner with a hydrohalogenating agent, such as N-bromosuccinimide, N-chlorosuccinimide or N-iodosuccinimide. Although temperature and pressure are not critical in this procedure, a temperature of between about 0°C. and room temperature (22°C.), especially between about 0°C. and 5°C., and atmospheric pressure are preferred. The resulting halohydrin can then be converted in a conventional manner into an epoxide of formula I by dissolving the halohydrin in a conventional inert organic solvent, preferably an alcohol, particularly methanol, when X is an oxymethylene group (which can carry a lower alkyl, lower alkenyl or lower alkynyl group), and preferably an ether, particularly diethyl ether, when X is a carboxylic acid grouping, and treating the solution with a base. When the halohydrin is dissolved in an alcohol, the base preferably is an alkali metal alcoholate, especially sodium methylate, and when the halohydrin is dissolved in an ether, the base preferably is a powdered alkali metal hydroxide, especially potassium hydroxide. Although temperature and pressure are not critical in the dehydrohalogenation, a temperature of between about 0°C. and 40°C. and atmospheric pressure are preferably utilized.

In obtaining an epoxy-polyene compound of formula I, the procedure described in the preceding paragraph, involving forming and then dehydrohalogenating a halohydrin, offers the advantage that, in the case of esters and ethers, only the terminal double bond is epoxidized. The epoxidation of polyene compounds with a peracid does not, in general, selectively lead to a corresponding epoxide. Rather, there is usually obtained a mixture of epoxides which can be separated by chromatography in a manner known per se.

A third method for obtaining a polyene ester, nitrile or amide of this application involves reacting the carbonyl compound of formula IIA or VII with the compound of formula XI or XIII to give a hydroxy-compound of formula XII or XIV and then dehydrating the resulting hydroxy-compound of formula XII or XIV. This procedure can be carried out in a conventional manner by initially forming the organo-metallic compound of formula XI or XIII in situ. for this purpose, the corresponding bromo compound of formula XI or XIII is initially dissolved in an inert organic solvent, containing the carbonyl compound of formula IIA or VII. The resulting solution is then treated in a conventional manner with zinc granules, which may be activated in a conventional manner by pre-treatment with acid and/or iodine. In this reaction, any conventional inert organic solvent may be utilized, such as benzene, toluene, diethyl ether, dioxane or tetrahydrofuran. In this reaction, although temperature and pressure are not critical, the reaction is preferably carried out at a temperature between room temperature and reflux, especially reflux, and at atmospheric pressure. The organometallic compound of formula XI or XIII, which is formed thereby in situ, reacts with the carbonyl compound of formula IIA or VII to form an organometallic complex compound, which is decomposed to a hydroxy compound of formula XII or XIV by the addition of water. The organic phase is then separated, dried and evaporated. The hydroxy compound can be dehydrated in a conventional manner. Preferably, the dehydration is carried out by treating the hydroxy-compound with acid, preferably with acetic acid in the presence of sodium acetate and water with warming.

A method preparing a polyene carbamate of this application involves reacting the alcohol of formula XV with the compound of formula XVI to give a corresponding carbamate. The reaction is carried out in a conventional inert organic solvent, such as acetone or methylene chloride, in the presence of small amounts of a conventional electron donor, such as triethylamine or piperidine. In this reaction, temperature and pressure are not critical, and the reaction can be suitably carried out at room temperature and atmospheric pressure.

A method for obtaining the polyene aldehydes of this application involves oxidizing the alcohol of formula XV in a conventional manner with manganese dioxide. This reaction can be suitably carried out by dissolving alcohol of formula XV in a conventional, inert organic solvent, such as petroleum ether, chloroform, methylene chloride or benzene, and shaking the solution with activated manganese dioxide. Although temperature and pressure are not critical in this reaction, a temperature between about 0°C. and the reflux temperature of the mixture, especially room temperature, and atmospheric pressure are preferably utilized. The resulting inorganic precipitate is separated, and the desired product isolated by evaporation in a conventional manner.

Another method for obtaining the polyene esters of this application involves reacting the acid of formula XVII with a lower alkyl, lower alkenyl or lower alkynyl halide, preferably a bromide, of formula XVIII in the presence of a base in a conventional manner.

Still another method for obtaining the polyene esters of this application involves converting the acid of formula XVII to the corresponding acid halide and then reacting the acid halide with the alcohol of formula XVIIIA. The acid of formula XVII can be converted to the corresponding acid halide by dissolving it in a conventional, inert organic solvent, such as petroleum ether, benzene, or hexane, to which is added a conventional acid binding agent, such as pyridine, triethylamine, or quinoline, preferably pyridine, and treating the acid with a halogenating agent such as thionyl chloride, phosphorus trichloride, thionyl bromide, or phosphorus oxychloride, preferably thionyl chloride. The resulting acid halide can then be reacted with the alcohol of formula XVIIIA in a conventional inert organic solvent, such as benzene, toluene, hexane, isooctane, chloroform, carbon tetrachloride or ethyleneglycol dimethyl ether, in the presence of a conventional acid binding agent, such as are set forth above. In this procedure, temperature and pressure are not critical, and room temperature and atmospheric pressure can be suitably utilized.

Another method for obtaining the polyene amides of this application involves reacting the acid halide, formed as set forth above, with the amine of formula XIX in a conventional manner.

A method for obtaining the polyene ketones of this application involves reacting the acid of formula XVII with two (2) equivalents of an organo-lithium compound of formula XX in a conventional, inert organic solvent, such as diethyl ether. Although temperature and pressure are not critical in this reaction, temperatures between about 0°C. and the boiling of the reaction mixture, especially temperatures between about room temperature and the boiling temperature, and atmospheric pressure are preferred. The reaction mixture is expediently worked-up by treatment treated with an aqueous ammonium chloride solution, separation of the organic phase and evaporated. The desired product can be purified in a conventional manner.

A method for obtaining the hydroxy- and alkoxy-polyene compounds of this application involves reacting a polyene compound of formula I, in which A and B taken together form a carbon to carbon double bond, with water or a lower alkanol, preferably methanol or ethanol. This reaction is carried out in the presence of an acid, preferably a mineral acid such as, for example, sulphuric acid. A conventional, inert organic solvent, preferably tetrahydrofuran, is expediently used as a solvent. Although temperature and pressure are not critical in this reaction, the reaction is preferably carried out between about 0°C. and the reflux temperature of the reaction mixture, especially between about 0°C. and 40°C., and at atmospheric pressure. Polyene compounds of formula I in which A is hydroxy or lower alkoxy are thus obtained. An especially preferred procedure is that described in J. Am. Chem. Soc. 91, 5646 (1969). This procedure involves reacting the polyene compound of formula I with water or an appropriate alcohol in the presence of a mercury salt. The organomercury compound formed as an intermediate in this process can subsequently be reduced, without isolating this intermediate, by treating it with a reducing agent. Suitable mercury salts include mercury acetate and other acylates, mercury nitrate, mercury trifluoroacetate and mercury halides. Suitable reducing agents include the alkali metal borohydrides, hydrazine and sodium amalgam. Treatment of the polyene compound of formula I, as described above, provides the polyene compound of formula I in which A is hydroxy (when treatment with water) or lower alkoxy (when treatment with an alkanol) and B is hydrogen.

The hydroxy-polyene compound of formula I, obtained by the procedure described above, can be etherified in a conventional manner with a compound of formula XXI to form an alkoxy-polyene compound of formula I, wherein A is lower alkoxy. This etherification can be carried out in the same manner as previously described for the reaction of a compound of formula IX with a compound of formula X, in which J is chlorine, bromine, iodine, or tosyloxy.

The polyene thioesters of this application can be obtained in a conventional manner by reacting the acid halide, derived from the acid of formula XVII in the manner set forth above, with the lower alkanethiol, lower alkenethiol or lower alkynethiol of formula XXII in a conventional manner.

The polyene nitriles of this application can be obtained in a conventional manner by reacting the carbonyl compound of formula V with the phosphonacetonitrile of formula XXIII in the presence of a base, such as an alkali metal hydride or alkoxide, in an inert organic solvent such as tetrahydrofuran, dimethylsulfoxide, toluene, diethyl ether and dimethylformamide.

The carbonyl compounds of formula II, wherein $n$ is 1, can be obtained by reacting a ketal of the formula:

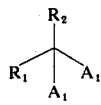  XXIV wherein
R₁ and R₂ are lower alkyl; and
each of A₁ is lower alkoxy;
with a vinyl ether of the formula:

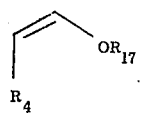  XXV wherein
R₄ is hydrogen or lower alkyl; and
R₁₇ is lower alkyl.

This reaction can be carried out in a conventional manner in the presence of a Lewis acid such as, for example, boron trifluoride (used in the form of the etherate), zinc chloride or ferric chloride. This reaction is preferably carried out in the absence of a solvent. However, if desired, a conventional inert organic solvent can be utilized. Although, in this reaction, temperature and pressure are not critical, a temperature between 0°C. and room temperature and atmospheric pressure are preferably utilized.

There is thus obtained an acetal of the formula:

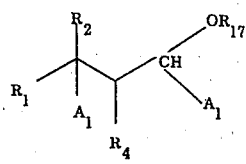  XXVI wherein R₁, R₂, R₄, R₁₇ and A₁ are as above.

The acetals of formula XXVI can be converted to the aldehydes of formula II by conventional acid hydrolysis, such as by treating the acetal with 5% phosphoric acid. The acid hydrolysis can be expediently carried out by warming the mixture of acetal and acid to about 60°–100°C. in the presence of a small amount of hydroquinone. There is thus obtained an aldehyde of the formula:

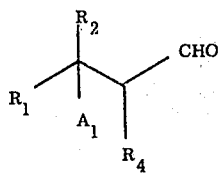  XXVII wherein R₁, R₂, R₄ and A₁ are as above.
An α,β-unsaturated aldehyde of the formula:

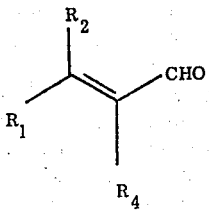  XXVIII wherein R₁, R₂ and R₄ are as above;
can be obtained in a conventional manner by pyrolyzing a vinyl ether of formula XXV in the presence of an acid catalyst such as p-toluenesulfonic acid of ammonium dihydrogen phosphate, or by warming the vinyl ether at 50°–100°C. in a dilute aqueous mineral acid such as 10% hydrochloric acid.

An aldehyde of the formula:

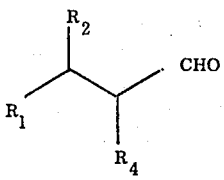  XXIX wherein R₁, R₂ and R₄ are as above;
can be obtained by hydrogenating an α,β-unsaturated aldehyde of formula XXVIII. This reaction can be carried out catalytically in a conventional, inert organic solvent, such as ethyl acetate or methanol. In this reaction, temperature and pressure are not critical, and a temperature between about room temperature and the boiling temperature of the solvent and a normal or elevated pressure can be suitable utilized. In this reaction, conventional hydrogenation catalysts can be utilized, such as Raney-nickel or a noble metal such as platinum or palladium, preferably palladium on calcium carbonate.

Aldehydes of the formula:

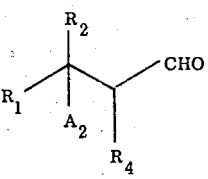  XXX wherein A₂ is lower alkyl; and
R₁, R₂ and R₄ are as above;
can be prepared by reacting an α,β-unsaturated aldehyde of formula XXVIII with a compound of the formula:

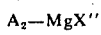

wherein

X'' is chlorine, bromine or iodine; and

A$_2$ is as above;

in the presence of cuprous salts (such as cuprous chloride) or with an organo-copper complex of the formula:

  XXXII wherein

A$_2$ is as above;

Cu is copper; and

Li is lithium.

This reaction can be carried out in a conventional manner in an ether, preferably diethyl ether or tetrahydrofuran, at a temperature between about −30°C. and 0°C. The preparation of the organo-copper complex can be carried out as described, for example, in J. Org. Chem. 31, 3128 (1966).

Hydroxyacetals of the formula

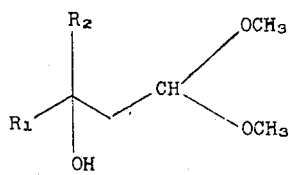  XXXIII wherein R$_1$ and R$_2$ are as above;

are useful intermediates in preparing alkoxy polyenes of formula I. The hydroxyl group in the hydroxyacetal of formula XXXIII can be etherified with a lower alkyl halide in the same manner as described hereinbefore for the reaction of, for example, a compound of formula IX in which K is —OM with a corresponding compound of formula X.

The hydroxyacetal of formula XXXIII can be obtained, according to the method described in Chem. Abstr. 51, 2854 (1957), by reacting a compound of the formula:

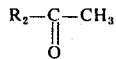  XXXIV wherein R$_2$ is as above;

with methyl formate in methanol. The resulting compound of formula:

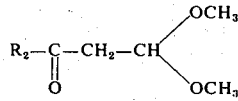  XXXV wherein R$_2$ is as above;

is then reacted in a manner known per se with a compound of the formula:

  XXXVI wherein R$_1$ is as above.

There is thus obtained, (optionally after conventional etherification of the hydroxyl group) after conventional acidic hydrolysis of the acetal function, an aldehyde of the formula:

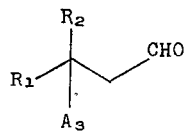  XXXVII wherein A$_3$ is hydroxy or lower alkoxy; and R$_1$ and R$_2$ are as above:

The aldehydes of formulae XXVII, XXVIII, XXIX, XXX and XXXVII can be generically formulated thus:

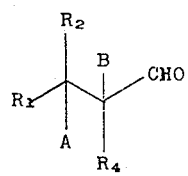  XXXVIII wherein R$_1$, R$_2$, R$_4$, A and B are as above.

From an aldehyde of formula XXXVIII, there can be obtained as described above, polyene compounds of formula I wherein $n$ is zero.

Carbonyl compounds of formula II, in which $n$ is 1, can be prepared by reacting an aldehyde of the formula

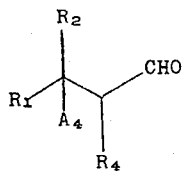  XXXIX wherein R$_1$, R$_2$ and R$_4$ are as above; and A$_4$ is hydrogen, hydroxy, lower alkoxy or lower alkyl, with a phosphine oxide of the formula:

XL wherein R$_3$ is as above;

to give a compound of the formula:

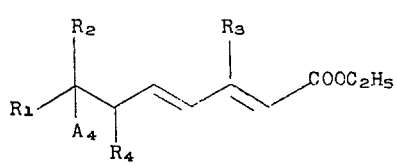

XLI wherein $R_1$, $R_2$, $R_3$, $R_4$ and $A_4$ are as above.
This reaction can be carried out in a conventional manner as described above in connection with other Horner reactions.

The compound of formula XLI can be catalytically hydrogenated in a conventional manner, to form a corresponding perhydrogenated compound. This hydrogenation reaction can be carried out in an inert organic solvent, such as ethyl acetate or methanol. In this hydrogenation, temperature and pressure are not critical, and the reaction can be suitably carried out at a temperature between room temperature and the boiling temperature of the solvent and at a normal or elevated pressure. Suitable catalysts are, for example, Raney nickel or noble metals, such as platinum or palladium.

The resulting perhydrogenated compound can be converted to the corresponding alcohol by dissolving the perhydrogenated compound, according to its solubility properties, in a conventional inert organic solvent and treating it with a hydride reducing agent. Among the solvents which can be utilized are, for example, tetrahydrofuran, dioxane, diethyl ether, hexane, toluene or xylene, preferably benzene where a (lower alkoxy)-(lower alkylenoxy)-alkali metal aluminum hydride is used as the reducing agent and preferably diethyl ether or tetrahydrofuran where an alkali metal aluminum hydride is used as the reducing agent. The reducing agent is preferably added in benzene solution. It is generally sufficient to add the hydride reducing agent in equimolar amount, although it can occasionally be advantageous to use the hydride reducing agent in about 10–20 percent excess. In this reaction, temperature and pressure are not critical. According to the nature of the ester used, the reduction is preferably carried out at a temperature between −70° and +80°C and at atmospheric pressure. A temperature between 0°C and 20°C is particularly preferred.

The alcohol prepared according to the preceding paragraph can be oxidized with chromium trioxide in pyridine in a conventional manner preferably between 0°C and room temperature, to give an aldehyde of the formula:

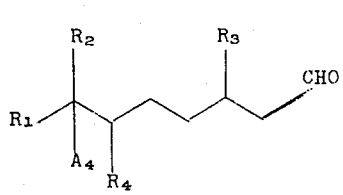

XLII wherein $R_1$, $R_2$, $R_3$, $R_4$ and $A_4$ are as above

The aldehydes of formula XLII can also be prepared from aldehydes of formula XXXIX by reaction with a phosphorane of the formula:

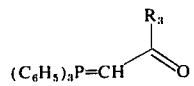

XLIII wherein $R_3$ is as above;
by means of a conventional Wittig reaction, utilizing the conditions described above. There is thus obtained a compound of the formula:

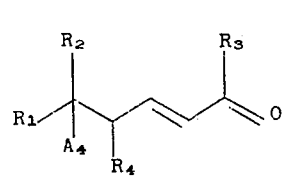

XLIV wherein $R_1$, $R_2$, $R_3$, $R_4$ and $A_4$ are as above.
The compound of formula XLIV can be catalytically hydrogenated in a conventional manner, as described above, to give a compound of the formula:

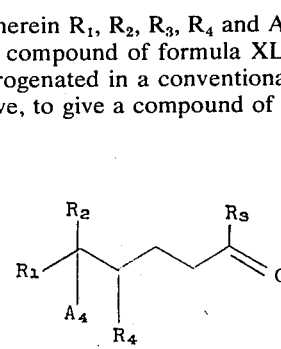

XLV wherein $R_1$, $R_2$, $R_3$, $R_4$ and $A_4$ are as above.
The compound of formula XLV can be converted by means of a conventional Horner reaction, as described above, with a phosphine oxide of the formula:

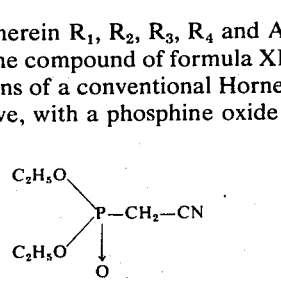

XLVI into a nitrile of the formula:

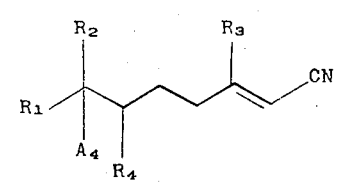

XLVII wherein $R_1$, $R_2$, $R_3$, $R_4$ and $A_4$ are as above,

The nitrile of formula XLVII can be converted into the corresponding aldehyde by dissolving the nitrile in a conventional inert organic solvent, such as tetrahydrofuran, petroleum ether, benzene or hexane and treating it with a reducing agent, such as diisobutyl aluminum hydride, dissolved in an organic solvent, preferably benzene. This reaction can be carried out in a conventional manner under a protective gas atmosphere, perferably nitrogen, at 0°C to room temperature. After termination of the reaction, isopropanol and dilute ammonium chloride solution are added to the reaction mixture, with cooling in order to decompose the organometallic complex formed. Subsequent treatment with dilute mineral acid, preferably dilute sulphuric acid, yields, after a conventional work-up, an aldehyde of the formula:

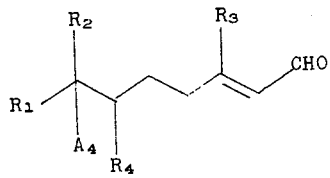

XLVIII wherein $R_1$, $R_2$, $R_3$, $R_4$ and $A_4$ are as above.

The catalytic reduction of the aldehyde of formula XLVIII in a conventional manner, as described above, yields an aldehyde of formula XLII.

The aldehyde of formula XLII, in which $A_4$ is hydroxy or lower alkoxy, can be converted in a conventional manner into an aldehyde of the formula:

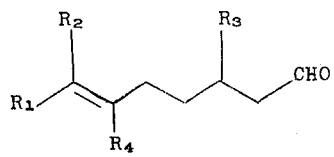

IL.

wherein $R_1$, $R_2$, $R_3$ and $R_4$ are as above;
by elimination of water or a lower alkanol. This elimination can be carried out by, for example, mixing the aldehyde of formula XLII with a strong acid, such as oxalic, hydrochloric or sulfuric acid, preferably 85 percent phosphoric acid, optionally in a conventional inert organic solvent, and warming the mixture at 100°C to 200°C.

The aldehyde of formula XLII or IL can be reacted by means of a conventional Horner reaction, as described above, with a phosphine oxide of formula XLVI to give a nitrile of the formula:

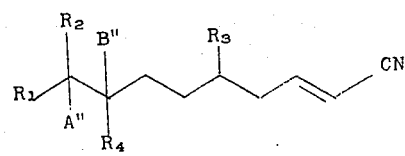

L wherein $R_1$, $R_2$, $R_3$, $R_4$, A″ and B″ are as above.

The nitrile of formula L can be reduced in a conventional manner, as described above, to the corresponding aldehyde, by treatment with diisobutyl aluminum hydride and subsequent acid treatment. The resulting aldehyde is of the formula:

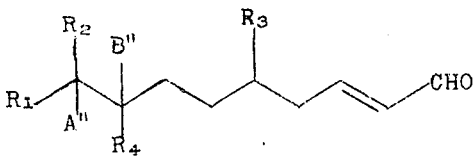

LI wherein $R_1$, $R_2$, $R_3$, $R_4$, A″ and B″ are as above.

Utilizing the above described procedure for obtaining an aldehyde of formula LI from an aldehyde of formula XXXIX, an aldehyde of formula:

LII wherein $R_1$, $R_2$, $R_4$, A″ and B″ are as above;
can be converted to an aldehyde of the formula:

LIII wherein $R_1$, $R_2$, $R_4$, A″ and B″ are as above.

Aldehydes of formulae IL, LI and LIII can, if desired and when A″ and B″ taken together form a carbon to carbon double bond, be epoxidized in a conventional manner, as described above.

Alcohols corresponding to the starting materials of formula XV can be obtained in a conventional manner, by reducing a lower alkyl ester of the formula:

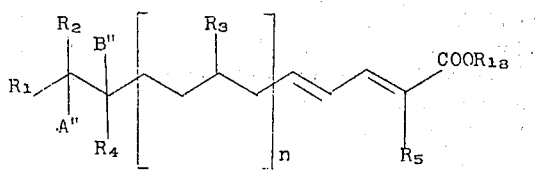

LIV wherein $R_1$, $R_2$, $R_3$, $R_4$, $R_5$, $A''$, $B''$ and $n$ are as above; and $R_{18}$ is lower alkyl;

with a (lower alkoxy)-(lower alkylenoxy)-alkali-aluminum hydride or an alkali metal aluminum hydride, preferably bis (methoxy-ethylenoxy)-sodium-aluminum hydride or lithium aluminum hydride. A preferred embodiment of this reduction has been described above.

The resulting alcohol of formula XV can, if desired, be epoxidized and/or converted into a halide of formula IX, in which K is chlorine, bromine or iodine.

The conversion of the alcohol into the halide of formula IX, can be carried out in a conventional manner by dissolving the alcohol in a conventional inert organic solvent, such as petroleum ether, benzene, hexane or, preferably, tetrahydrofuran and treating it with a halogenating agent, such as phosphorus trichloride, thionyl bromide, phosphorus oxychloride or, preferably, thionyl chloride in the presence of an acid binding agent, such as triethylamine, quinoline or, preferably, pyridine.

The acid starting material of formula XVII can be prepared in a conventional manner by the alkaline saponification of an ester of formula I. The use of such acid starting materials is preferred for the formation of esters of formula I which are relatively inaccessable by reesterification procedures.

The polyene compounds of formula I are obtained as cis/trans isomeric mixtures. Such mixtures can be separated into the isomeric forms by, for example, adsorption on a material with selective activity. Conventional adsorption procedures can be utilized, involving dissolving the isomeric mixture in an inert organic solvent such as hexane, diethyl ether or ethyl acetate and adsorbing the mixture on Kieselgel. The isomers which are adsorbed in different zones can be eluted with one of the aforementioned solvents and isolated. The isomeric mixtures can also be separated, in certain cases, by fractional distillation or by conventional preparative gas chromatography or preparative thin layer chromatography.

The experiments which follow further illustrate this invention.

EXAMPLE 1

62.4 g of tetrahydrocitral and 113.3 g of 1-carbomethoxy-1-propenyl-diethylphosphonate are dissolved in 200 ml of benzene. A solution (cooled to 0°C.) of 11.0 g of sodium in 120 ml of methanol is subsequently added dropwise within 1 hour, and the mixture is stirred overnight (16 hours) at room temperature (about 22°C.). The mixture is poured on to ice and extracted with diethyl ether. The ethereal phase is washed to neutrality (pH of about 7), dried and evaporated. The crude product is chromatographed on 600 g of Kieselgel, using hexane/5% by volume diethyl ether as the eluant. There is obtained, as a colorless liquid, 7,11-dimethyl-2,4-dodecadienoic acid methyl ester; boiling point 105°C/0.065 mmHg; $n_D^{20} = 1.4478$.

EXAMPLE 2

Utilizing the procedure of Example 1, citronellal and 1-carbomethoxy-1-propenyl-diethylphosphonate are converted to 7,11-dimethyl-2,4,10-dodecatrienoic acid methyl ester, obtained as a colorless oil; boiling point 85°C/0.05 mmHg (bulb tube); $n_D^{25} = 1.5009$.

EXAMPLE 3

Utilizing the procedure of Example 1, 3,7-dimethyl-7-methoxy-octan-1-al and 1-carbomethoxy-1-propenyl-diethylphosphonate are converted to 7,11-dimethyl-11-methoxy-2,4-dodecadienoic acid methyl ester, obtained as a colorless oil; boiling point 145°–150°C/0.085 mmHg; $n_D^{25} = 1.4842$.

EXAMPLE 4

Utilizing the procedure of Example 1, 3,6,7-trimethyl-octan-1-al and 1-carbomethoxy-1-propenyl-diethylphosphonate are converted to 7,10,11-trimethyl-2,4-dodecadienoic acid methyl ester, obtained as a colorless liquid; boiling point 95°C/0.002 mmHg (bulb tube); $n_D^{20} = 1.4727$.

EXAMPLE 5

11.2 g of 3,6,7-trimethyl-6-octenal is dissolved in 120 ml of ethyl acetate and mixed with 2 g of palladium (10% by wt.) on calcium carbonate and 0.3 of platinum oxide. The mixture is stirred at room temperature (22°C.) under an atmosphere of hydrogen. The course of the hydrogenation is followed by removing samples and subjecting them to gas chromatography. The hydrogenation is terminated when the starting material can no longer be detected by gas chromatography. The product is filtered through Celite diatomaceous earth and concentrated on a rotary evaporator. The resulting oil is purified by chromatography on a 10-fold amount of Kieselgel, using 1% by volume diethyl ether in hexane as the eluant. There is obtained 3,6,7-trimethyl-octan-1-al as a colorless oil; $n_D^{25} = 1.4436$.

EXAMPLE 6

2.4 g of 7,11-dimethyl-2,4,10-dodecatrienoic acid methyl ester is dissolved in 30 ml of methylene chloride and mixed portionwise at 0°C., with stirring, with 2.4 g of m-chloroperbenzoic acid (ca 80% by wt.). Subsequently the mixture is stirred for a further 1.5 hours at 0°C. The mixture is poured on to ice, treated with 1-N sodium hydroxide, and extracted with diethyl ether. The ethereal phase is washed to neutrality, dried and evaporated. The product is chromatographed on a 50-fold amount of Kieselgel, using hexane/20% by volume ethyl acetate as the eluant. There is obtained 10,11-epoxy-7,11-dimethyl-2,4-dodecadienoic acid methyl ester, as a colorless oil; boiling point ca. 62°C/0.05 mmHg (bulb tube); $n_D^{25} = 1.4958$.

EXAMPLE 7

1.6 g of 3,7-dimethyl-2,4-dodecadienoic acid is dissolved in 20 ml of absolute diethyl ether and 0.55 ml of pyridine. The resulting mixture is added dropwise over a period of about 10 minutes to 0.57 ml of thionyl chloride at a temperature between 0°C. and +10°C. Subsequently the mixture is stirred for 1 hour at room temperature (22°C.), then decanted off, and the residue is washed with absolute diethyl ether. The solution is evaporated to dryness under anhydrous conditions. The residue is dissolved in 10 ml of absolute diethyl ether. The ethereal solution is added dropwise at a temperature between 0°C. and +10°C., over a period of about 20 minutes, to a solution consisting of 0.56 ml of propargyl alcohol and 0.55 ml of pyridine in 10 ml of absolute ether. After stirring overnight (16 hours) at room temperature (22°C.) the mixture is diluted with diethyl ether, washed with 1-N hydrochloric acid, saturated aqueous sodium bicarbonate solution and finally with aqueous sodium chloride solution. After drying, the ethereal phase is evaporated. The crude product is chromatographed on a 30-fold amount of Kieselgel, using hexane/diethyl ether (19:1 parts by volume) as the eluant. There is obtained 3,7-dimethyl-2,4-dodecadienoic acid propargyl ester as a colorless oil; boiling point 105°C/0.05 mmHg (bulb tube); $n_{25}$ 25= 1.4951.

EXAMPLE 8

Utilizing the procedure of Example 7, 7,11-dimethyl-11-methoxy-2,4-dodecadienoic acid and propargyl alcohol are converted to 7,11-dimethyl-11-methoxy-2,4-dodecacidienoic acid propargyl ester, obtained as a colorless oil; boiling point 135°C/0.05 mmHg (bulb tube); $n_D^{20} = 1.4992$.

EXAMPLE 9

Utilizing the procedure of Example 7, 7,11-dimethyl-11-methoxy-2,4-dodecadienoic acid and isopropanol are converted to 7,11-dimethyl-11-methoxy-2,4-dodecadienoic acid isopropyl ester, obtained as colorless oil; boiling point 150°C/0.05 mmHg (bulb tube); $n_D^{20} = 1.4800$.

EXAMPLE 10

2.3 g of 7,11-dimethyl-2,4-dodecadienoic acid methyl ester is dissolved in 46 ml of methanol and 18 ml of tetrahydrofuran. The mixture is cooled to 0°C., and 4.9 g of potassium hydroxide in 18 ml of water is added. The mixture is stirred overnight (18 hours) at room temperature (22°C.), poured on to water, and extracted with diethyl ether. The aqueous phase is made slightly acidic with 3-N sulphuric acid and again extracted with diethyl ether. The latter, ether extract is washed to neutrality, dried and evaporated. There is obtained 7,11-dimethyl-2,4-dodecadienoic acid, obtained as a slightly-yellow, colored oil, which is uniform according to thin-layer chromatography and which can be utilized without further processing.

EXAMPLE 11

Utilizing the procedure of Example 10, 7,11-dimethyl-2,4,10-dodecatrienoic acid methyl ester is converted to 7,11-dimethyl-2,4,10-dodecatrienoic acid. The thin-layer chromatographically uniform, yellowish oil can be utilized without further processing.

EXAMPLE 12

Utilizing the procedure of Example 10, 7,10,11-trimethyl-2,4-dodecadienoic acid methyl ester is converted to 7,10,11-trimethyl-2,4-dodecadienoic acid. The thin-layer chromatographically uniform, yellowish oil can be utilized without further processing.

EXAMPLE 13

29.5 g of 3,7-dimethyl-7-methoxy-octanal and 42 g of diethylphosphono-α-methyl-crotonic acid methyl ester are dissolved in 100 ml of absolute benzene. To this solution there is added dropwise 4.1 g of sodium dissolved in 50 ml of absolute methanol. The mixture is stirred for 5 hours at 60°C., poured on to ice-water and extracted with diethyl ether. The ethereal solution is washed with water, then with aqueous sodium bicarbonate solution and once again with water, dried with sodium sulphate, filtered and concentrated on a rotary evaporator. After chromatography on a 30-fold amount of Kieselgel, using hexane/diethyl ether (9:1 parts by volume) as the eluant, there is obtained 11-methoxy-2,7,11-trimethyl-2,4-dodecadienoic acid methyl ester; boiling point 100°C/0.002 mmHg.

EXAMPLE 14

24 g of citronellal and 40 g of diethylphosphono-α-methylcrotonic acid methyl ester are dissolved in 100 ml of absolute benzene. To this solution there is added dropwise 4 g of sodium in 50 ml of absolute methanol. The mixture is stirred for 5 hours at 60°C., poured on to ice-water and extracted with diethyl ether. The ethereal solution is washed with water, then with aqueous sodium bicarbonate solution and once again with water, dried over sodium sulphate, filtered and concentrated on a rotary evaporator. After chromatography on a 30-fold amount of Kieselgel, using hexane/diethyl ether (9:1 parts by volume) as the eluant, there is obtained 2,7,11-trimethyl-2,4,10-dodecatrienoic acid methyl ester; boiling point 95°C/0.001 mmHg.

EXAMPLE 15

3.7 g of 2,7,11-trimethyl-2,4,10-dodecatrieonoic acid is dissolved in 100 ml of methyl ethyl ketone and then mixed with 3 g of potassium carbonate and 3 g of ethyl bromide. The mixture is boiled under reflux for 3 hours, then added to cold water and extracted with diethyl ether. The ethereal phase is washed to neutrality, dried and evaporated. There is obtained 2,7,11-trimethyl-2,4,10-dodecatrieonoic acid ethyl ester; boiling point 105°C/0.001 mmHg.

EXAMPLE 16

Utilizing the procedure of Example 15, 11-methoxy-2,7,11-trimethyl-2,4-dodecatrienoic acid and isopropyl bromide are reacted. After chromatography on Kieselgel, using diethyl ether/petroleum ether (1:4 parts by volume) as the eluant, there is obtained 11-methoxy-2,7,11-trimethyl-2,4-dodecadienoic acid isopropyl ester in pure form; boiling point 120°C/0.002 mmHg.

EXAMPLE 17

Utilizing the procedure of Example 15, 11-methoxy-2,7,11-trimethyl-2,4-dodecadienoic acid and propargyl bromide are reacted. After chromatography on Kieselgel, using diethyl ether/petroleum ether (1:3 parts by volume) as the eluant, there is obtained 11-methoxy-2,7,11-trimethyl-2,4-dodecadienoic acid propargyl ester in pure form; boiling point 110°C/0.002 mmHg.

EXAMPLE 18

22.8 g. of 2,7,11-trimethyl-2,4,10-dodecatrienoic acid methyl ester is dissolved in 150 ml of methanol and mixed with 22.8 g. of sodium hydroxide dissolved in 35 ml of water. The mixture is boiled under reflux for 3 hours, poured on to ice-water and extracted with diethyl ether. The ether extracts are discarded and the aqueous phase acidified with dilute sulphuric acid. The acidic aqueous solution is extracted with diethyl ether and the ether extract is washed repeatedly with aqueous sodium chloride solution, dried over sodium sulphate, filtered and concentrated on a rotary evaporator. There is obtained 2,7,11-trimethyl-2,4,10-dodecatrienoic acid.

EXAMPLE 19

Utilizing the procedure of Example 18, 11-methoxy-2,7,11-trimethyl-2,4-dodecadienoic acid methyl ester is converted to 11-methoxy-2,7,11-trimethyl-2,4-dodecadienoic acid.

EXAMPLE 20

15 g of 7,11-dimethyl-11-methoxy-2,4-dodecadienoic acid is dissolved in 100 ml of absolute benzene and 5.3 g of pyridine and treated dropwise at between 0°C. and 5°C. over a period of about 30 minutes with 15 ml of thionyl chloride. Subsequently, the mixture is stirred for 1 hour at room temperature (22°C.), the precipitate filtered off and washed with benzene. The solution is evaporated to dryness under anhydrous conditions. The only residue is dissolved in 50 ml of benzene and mixed at 5°C. with 8 g of ethylmercaptan and 5.3 g of pyridine. After stirring overnight (16 hours) at room temperature (22°C.), the mixture is filtered. The filtrate is diluted with diethyl ether and washed with 2-N hydrochloric acid, then with saturated, aqueous sodium bicarbonate solution and finally with water. After drying, the organic phase is evaporated. The crude product is chromatographed on a 30-fold amount of Kieselgel, using hexane/15% by volume diethyl ether as the eluant. There is obtained 7,11-dimethyl-11-methoxy-2,4-dodecadienoic acid thioethyl ester as a colorless oil; boiling point 120°C/0.01 mmHg (bulb tube); $n_D^{24} = 1.5138$.

EXAMPLE 21

3.5 g of 7,11-dimethyl-2,4-dodecadienoic acid and 3.9 g of p-toluenesulphonic acid chloride are dissolved with ice-cooling in absolute pyridine. The solution is left for about 15 minutes in the ice-bath, and then, 1.5 g of ethylmercaptan is added with stirring. After stirring for 3 hours at room temperature (22°C.), the pyridine is evaporated off on a rotary evaporator. The residue is taken up in 100 ml of diethyl ether and washed several times by shaking with water. After drying, the organic phase is evaporated. The crude product is chromatographed on a 30-fold amount of Kieselgel, using hexane/2% by volume diethyl ether as the eluant. There is obtained 7,11-dimethyl-2,4-dodecadienoic acid thioethyl ester as a colorless oil; boiling point 120°C/0.02 mmHg (bulb tube); $n_D^{24} = 1.5241$.

EXAMPLE 22

Utilizing the procedure of Example 21, isopropylmercaptan and 7,11-dimethyl-2,4-dodecadienoic acid are converted to 7,11-dimethyl-2,4-dodecadienoic acid thioisopropyl ester, obtained as a colorless oil; boiling point 125°C/0.02 mmHg (bulb tube); $N_D^{25} = 1.5186$.

EXAMPLE 23

Utilizing the procedure of Example 21, butylmercaptan and 2,7,11-trimethyl-2,4-dodecadienoic acid are converted to 2,7,11-trimethyl-2,4-dodecadienoic acid thiobutyl ester; boiling point 130°–132°C/0.02 mmHg (bulb tube).

EXAMPLE 24

Leaf roundels of potato plants, which carry an egg lay consisting of ca. 30 eggs, are placed in small plastic boxes on a moist base. The eggs are treated topically with $10^{-3}$ ml of a solution of a polyene compound of formula I in acetone ($10^{-x}$ g/egg lay) and incubated at 25°C. and 60% relative humidity until the larvae hatch. The freshly hatched larvae are fed with potato leaves and observed for 2 days. The result is expressed as the percentage reduction of the $F_1$ generation (larvae which are still alive for 2 days). The following Table gives the results obtained with representative polyene compounds of formula I.

Table

| Polyene compound | Concentration $10^{-x}$ g/lay | Reduction in $F_1$ generation in % |
|---|---|---|
| (structure) | 4 | 100 |
|  | 5 | 94 |
|  | 6 | 93 |
|  | 7 | 10 |
| (structure) | 4 | 100 |
|  | 5 | 100 |
|  | 6 | 100 |
|  | 7 | 13 |
| (structure) | 4 | 100 |
|  | 5 | 100 |
|  | 6 | 100 |
|  | 7 | 41 |
|  | 8 | 7 |
| (structure) | 4 | 100 |
|  | 5 | 100 |
|  | 6 | 86 |
|  | 7 | 0 |
| (structure) | 4 | 100 |
|  | 5 | 100 |
|  | 6 | 90 |
|  | 7 | 13 |

We claim:
1. A polyene compound of the formula:

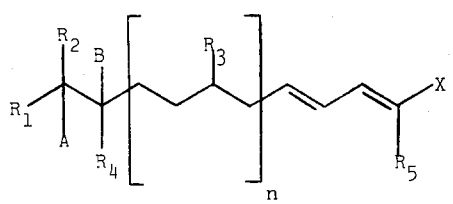

wherein $R_1$, $R_2$, and $R_3$ are methyl; $R_4$ is hydrogen or lower alkyl of 1–6 carbon atoms, and $R_5$ is hydrogen; A is individually hydrogen, hydroxy, lower alkoxy of 1–6 carbon atoms or lower alkyl of 1–6 carbon atoms; B is individually hydrogen; or A and B taken together form a carbon to carbon double bond or an oxygen bridge; X is —$COOR_6$ wherein $R_6$ is propargyl; and $n$ is equal to 1.

2. The compound of claim 1 wherein said compound is 7,11-dimethyl-2,4,10-dodecatrienoic acid propargyl ester.
3. The compound of claim 1 wherein A is hydrogen, lower alkoxy or lower alkyl and B is hydrogen.
4. The compound of claim 3 wherein A is lower alkoxy.
5. The compound of claim 4 wherein said compound is 11-methoxy-7,11-dimethyl-2,4-dodecadienoic acid propargyl ester.
6. The compound of claim 3 wherein A is lower alkyl.
7. The compound of claim 6 wherein said compound is 7,11,11'-trimethyl-2,4-dodecadienoic acid propargyl ester.
8. The compound of claim 1 wherein A and B are hydrogen.
9. The compound of claim 8 wherein said compound is 7,11-dimethyl-2,4-dodecadienoic acid propargyl ester.

* * * * *